US010149956B2

(12) United States Patent
Ure et al.

(10) Patent No.: US 10,149,956 B2
(45) Date of Patent: Dec. 11, 2018

(54) BI-LATERAL ENDOBRONCHIAL SUCTIONING DEVICE AND MEDICAL SUCTIONING SYSTEM FOR INTUBATED PATIENTS

(71) Applicants: John P. Ure, New Providence, NJ (US); Richard S. Teames, Pearland, TX (US)

(72) Inventors: John P. Ure, New Providence, NJ (US); Richard S. Teames, Pearland, TX (US)

( * ) Notice: Subject to any disclaimer, the term of this patent is extended or adjusted under 35 U.S.C. 154(b) by 889 days.

(21) Appl. No.: 14/634,803

(22) Filed: Feb. 28, 2015

(65) Prior Publication Data

US 2016/0250430 A1 Sep. 1, 2016

(51) Int. Cl.
*A61M 27/00* (2006.01)
*A61M 16/04* (2006.01)

(52) U.S. Cl.
CPC .... *A61M 16/0463* (2013.01); *A61M 16/0427* (2014.02); *A61M 16/0486* (2014.02); *A61M 16/0488* (2013.01); *A61M 2205/3375* (2013.01)

(58) Field of Classification Search
CPC .......... A61M 16/0463; A61M 16/0427; A61M 16/0486; A61M 16/0488
See application file for complete search history.

(56) References Cited

U.S. PATENT DOCUMENTS

| | | | |
|---|---|---|---|
| 3,606,889 A | 9/1971 | Arblaster | |
| 4,193,406 A | 3/1980 | Jinotti | |
| 4,453,545 A | 6/1984 | Inoue | |
| 4,507,118 A | 3/1985 | Dent | |
| 4,569,344 A | 2/1986 | Palmer | |
| 4,592,920 A | 6/1986 | Murtfeldt | |
| 4,623,329 A | 11/1986 | Drobish et al. | |
| 4,834,711 A | 5/1989 | Greenfield et al. | |
| 4,840,172 A | 6/1989 | Augustine et al. | |
| 5,140,983 A | 8/1992 | Jinotti | |
| 5,213,096 A | 5/1993 | Kihlberg et al. | |
| 5,215,522 A | 6/1993 | Page et al. | |

(Continued)

OTHER PUBLICATIONS

Popescu Wanda M.; Advancements in Lung Isolation Techniques; Anesthesiology News; Guide to Airway Management, pp. 37-45; 2014.

(Continued)

*Primary Examiner* — Ariana Zimbouski
(74) *Attorney, Agent, or Firm* — Eldredge Law Firm, LLC; Richard Eldredge; Beth Felix

(57) ABSTRACT

A bi-lateral endobronchial suctioning device includes actuating and articulating components that allow a provider to accurately suction both right and left bronchi as well as the trachea in a controlled and safe manner. A control mechanism is used to manipulate the actuating components in tubes forming a suction catheter to flex the tip of the bi-lateral endobronchial suctioning device to the left and to the right when the device is inserted through an endotracheal tube or other similar device, to enable directional control of a catheter for suctioning the lungs or trachea. The device further includes a bronchoalveolar lavage (BAL) port allowing sterile saline or other liquids or fluids to travel down the catheter lumen to assist with breaking up thick secretions which collect in the airways.

6 Claims, 14 Drawing Sheets

(56) References Cited

U.S. PATENT DOCUMENTS

| | | |
|---|---|---|
| 5,246,012 A | 9/1993 | Strickland |
| 5,254,098 A | 10/1993 | Ulrich et al. |
| 5,279,549 A | 1/1994 | Ranford |
| 5,300,043 A | 4/1994 | Devlin et al. |
| 5,325,850 A | 7/1994 | Ulrich et al. |
| 5,325,851 A | 7/1994 | Reynolds et al. |
| 5,349,950 A | 9/1994 | Ulrich et al. |
| 5,354,267 A | 10/1994 | Niermann et al. |
| 5,377,672 A | 1/1995 | Kee |
| 5,460,172 A | 10/1995 | Eckerbom et al. |
| 5,460,613 A | 10/1995 | Ulrich et al. |
| 5,490,503 A | 2/1996 | Hollister |
| 5,496,287 A | 3/1996 | Jinotti |
| 5,562,077 A | 10/1996 | Schultz |
| 5,624,704 A | 4/1997 | Darouiche et al. |
| 5,638,812 A | 6/1997 | Turner |
| 5,676,136 A | 10/1997 | Russo |
| 5,681,575 A | 10/1997 | Burrell et al. |
| 5,715,815 A | 2/1998 | Lorenzen et al. |
| 5,720,282 A | 2/1998 | Wright |
| 5,730,123 A | 3/1998 | Lorenzen et al. |
| 5,730,727 A | 3/1998 | Russo |
| 5,735,271 A | 4/1998 | Lorenzen et al. |
| 5,738,091 A | 4/1998 | Kee et al. |
| 5,775,325 A | 7/1998 | Russo |
| 5,779,687 A | 7/1998 | Bell et al. |
| 5,820,607 A | 10/1998 | Tcholakian et al. |
| 5,901,705 A | 5/1999 | Leagre |
| 6,012,451 A | 1/2000 | Palmer |
| 6,039,940 A | 3/2000 | Perrault et al. |
| 6,070,582 A | 6/2000 | Kee |
| 6,105,576 A | 8/2000 | Clawson et al. |
| 6,117,285 A | 9/2000 | Welch et al. |
| 6,415,788 B1 | 7/2002 | Clawson et al. |
| 6,588,425 B2 | 7/2003 | Rouns et al. |
| 6,923,184 B1 * | 8/2005 | Russo ............... A61M 16/0463 128/200.26 |
| 7,273,473 B2 | 9/2007 | Owens et al. |
| 7,478,636 B2 | 1/2009 | Madsen et al. |
| 8,453,648 B2 | 6/2013 | Black et al. |
| 2010/0113916 A1 | 5/2010 | Kumar |
| 2010/0170517 A1 | 7/2010 | Hackner |
| 2011/0023884 A1 | 2/2011 | Cuevas et al. |
| 2011/0313347 A1 | 12/2011 | Zocca et al. |
| 2012/0017914 A1 | 1/2012 | Watt et al. |
| 2012/0024292 A1 | 2/2012 | Sandmore et al. |
| 2013/0186407 A1 | 7/2013 | Hammer |
| 2016/0262601 A1 * | 9/2016 | Viebach ............... A61B 1/0125 |
| 2017/0072154 A1 * | 3/2017 | Hoftman ............ A61M 16/0816 |

OTHER PUBLICATIONS

Worthley; Bronchial Electrocardiography to Determine Left or Right Main Bronchial Placement; Intensive Care Medicine; vol. 19, Issue 2, pp. 96-98; 1993.

Placzek, M. and Silverman, M.; Selective Placement of Bronchial Suction Catheters in Intubated Neonates; Arch. Dis. Child; Jun. 27, 1983.

Kubota, Y. et al.; Evaluation of Selective Bronchial Suctioning in the Adult; CRI Care Medicine; Abstract; Dec. 1980.

\* cited by examiner

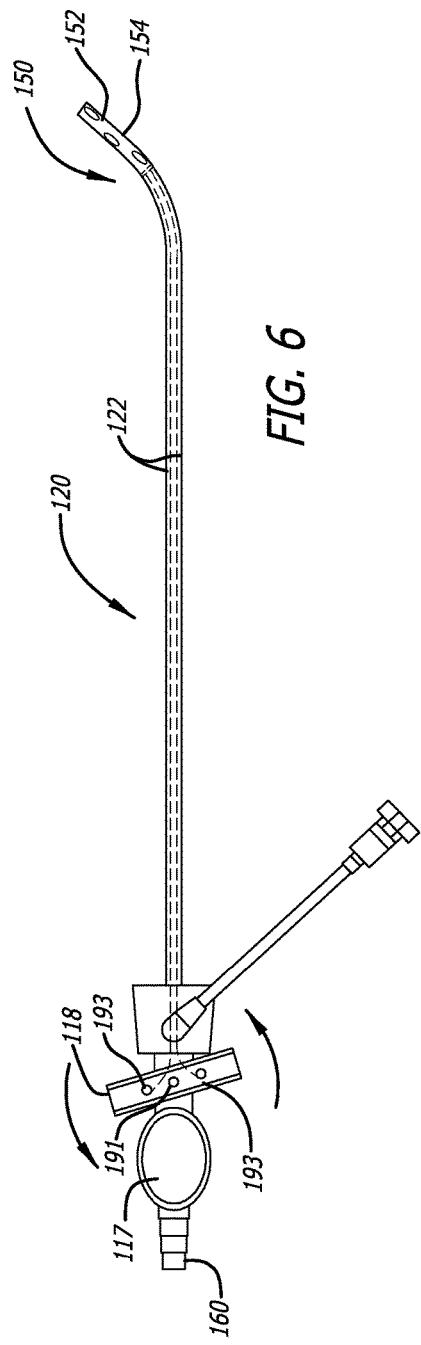
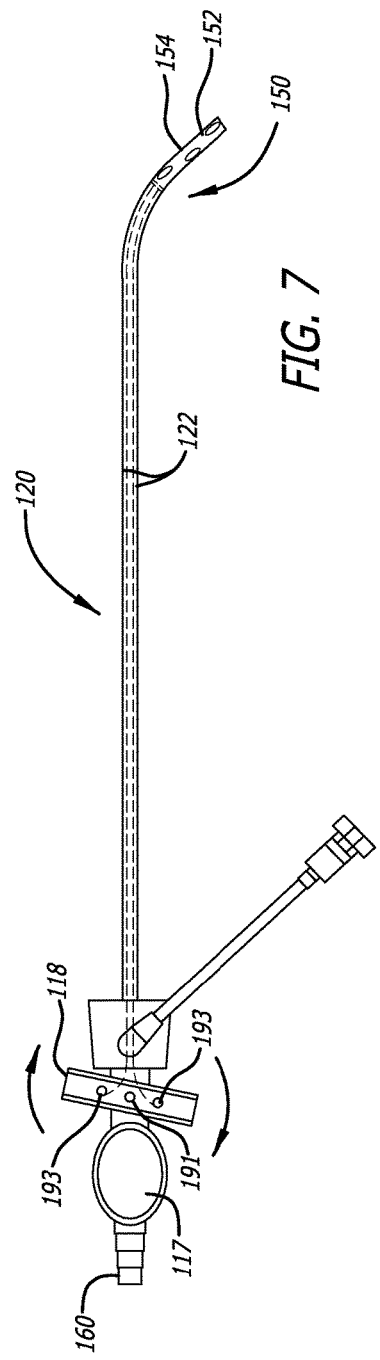

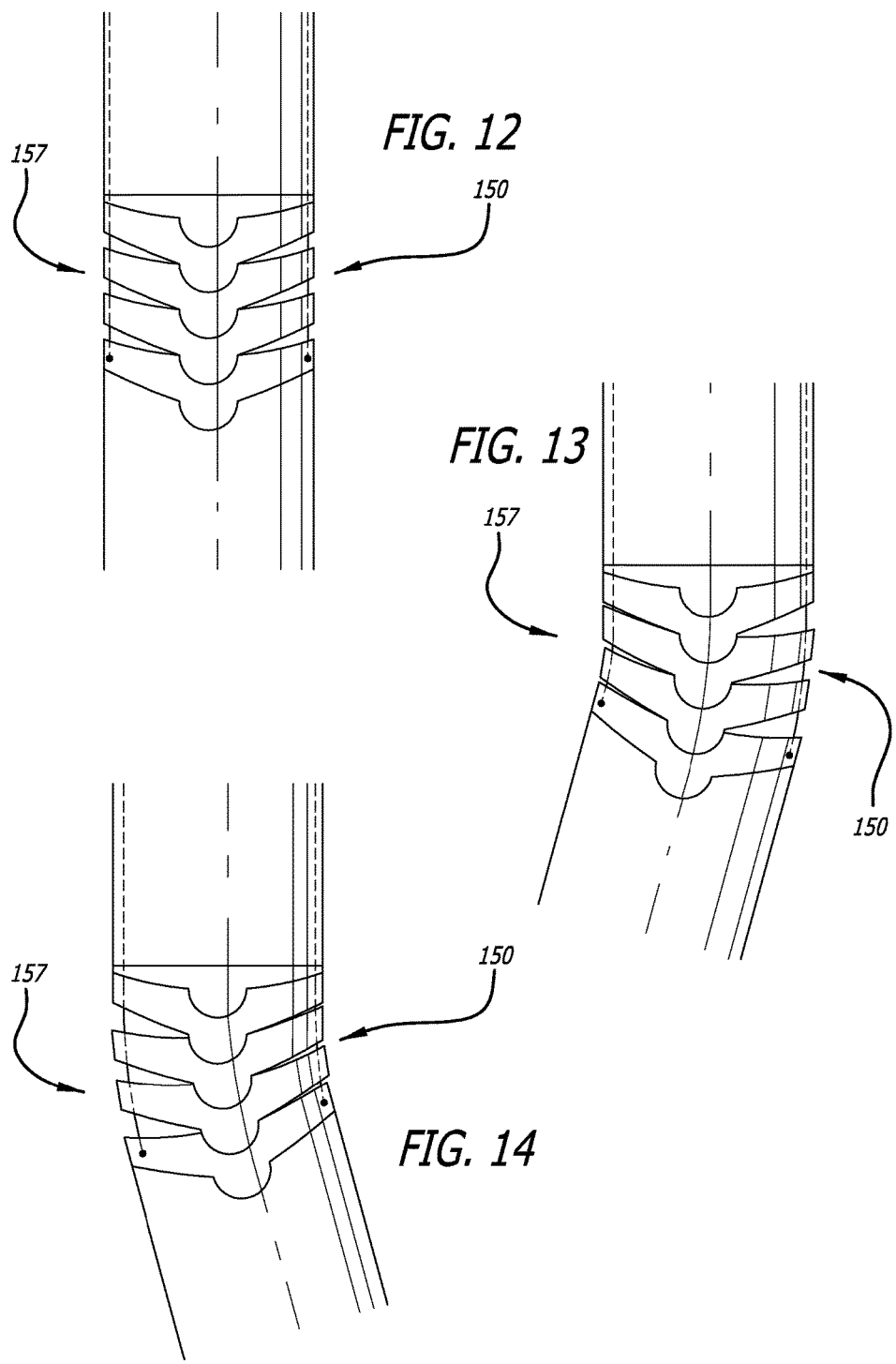

BI-LATERAL ENDOBRONCHIAL SUCTIONING DEVICE AND MEDICAL SUCTIONING SYSTEM FOR INTUBATED PATIENTS

FIELD OF THE INVENTION

The present invention relates to devices for suctioning devices for use in the field of medicine. Specifically, the present invention relates to a catheter for use with an endobronchial tube or the like that allows a provider to suction both right and left bronchi of the lungs as well as the trachea in a controlled and safe manner when a patient is intubated or has a tracheostomy tube.

BACKGROUND OF THE INVENTION

Intubated patients develop a pooling of secretions inside the bronchi of the lungs and in the trachea, and require frequent or constant suctioning to remove these secretions. Current processes utilize an unguided, directionless suction catheter which is inserted into an endotracheal tube (ETT) or tracheostomy tube (also known as a "trach") and is simply dropped into the lungs and pulled back slowly while suctioning. Because it is directionless, this existing device is less effective and has a tendency to leave fluid behind in one lung field or both.

Complicating the matter, the left bronchus connects to the trachea at a sharp angle (at about a 40 degree angle); this results in most suction catheters being dropped into the right bronchus (which connects to the trachea at only about a 15 degree angle). This leaves the left bronchus frequently un-suctioned, and if it remains in such a state, secretions can build up and may cause serious complications such as pneumonia or collapse of all or part of a lung field (atelectasis), and these may also propagate to a worsening of acute respiratory distress syndrome (ARDS) and/or septic pneumonia. These complications can require expensive and invasive actions, and prolonged intubation time and costs associated with extended stays in intensive care units of medical facilities such as hospitals.

Examples of existing technology for endotracheal suctioning devices may be found in U.S. Pat. No. 7,191,782, which discloses a suction catheter that may be adapted for removing fluid from a patient from application of negative pressure to a lumen of a tubular portion. Another example may be found in U.S. Pat. No. 5,246,012, which discloses a catheter for performing bronchoalveolar lavage comprising a sampling catheter so sized and configured as to extend from a bronchiole in the lung of a patient through the upper respiratory system. The assembly also includes means for directing the distal end of the sampling catheter into a preselected lung of the patient. Neither of these patents teach a control mechanism or lever for accurately guiding the distal end of the sampling catheter.

Another example of existing attempts to reach both bronchi of the lungs is found in U.S. Patent Publication No. 2011/0313347, which discloses a catheter that includes a distal end adapted to be introduced into the trachea and/or into the bronchi of a patient to suck up fluid secretions or other similar material. The distal end includes a viewing means that includes optical fibers suitable for transferring an image and a micro-camera or another visualization technology, and lighting means that includes other optical fibers suitable for guiding light. These enable the operator to identify the position of the distal end in the trachea and bronchial tree on a screen to ensure that the tube of the catheter is adjacent to or inside collections of fluid secretions. However, there is no mechanism for directional control of the device that allows for greater suctioning capability of the left bronchus.

BRIEF SUMMARY OF THE INVENTION

It is therefore one objective of the present invention to provide a system and method of enabling directional control of a device inserted into the body of an intubated patient. It is another objective of the present invention to provide a system and method of accurately suctioning the left bronchus of an intubated patient using an endotracheal or other similar device.

It is another objective of the present invention to provide a suction catheter that enables guided removal of secretions inside the bronchi, lungs, trachea and other parts of the body. It is yet another objective of the present invention to provide a system and method that reduces incidents of pneumonia, atelectasis, acute respiratory distress syndrome (ARDS), and other complications of re-intubation, unintended extubation, and premature extubation resulting from un-suctioned left bronchi or right bronchi or improperly suctioned left bronchi in patients. It is still another objective of the present invention to provide a device to the field of medicine that reduces patient intubation time and costs associated with extended stays in the intensive care units of medical facilities.

The present invention is an apparatus that allows the provider to suction both right and left bronchi of the lungs as well as the trachea in a controlled and safe manner. The apparatus is embodied in a bi-lateral endobronchial suctioning device (BESD) that is adapted for articulation through a tube such as an endotracheal tube or trach. The bi-lateral endobronchial suctioning device includes a control lever that allows a user to flex the tip of the device between the left and the right to suction both sides of the lungs. The bi-lateral endobronchial suctioning device therefore enables directional control of what would otherwise be a flimsy suctioning catheter.

The BESD also includes a bronchoalveolar lavage (BAL) port. This port allows sterile saline or other liquids or fluids to travel down the catheter lumen to, for example, assist with breaking up thick secretions which collect in the airways. In prior art devices, solutions such as sterile saline are simply squirted down the endotracheal tube, which gives no directional control over where the solutions are going, nor any intuitive way to remove it. With the BESD and suctioning system of the present invention, solutions such as sterile saline travel directly to the area of the airways that are to be suctioned, under the control of the provider.

Other objects, embodiments, features and advantages of the present invention will become apparent from the following description of the embodiments, taken together with the accompanying drawings, which illustrate, by way of example, the principles of the invention.

BRIEF DESCRIPTION OF THE SEVERAL VIEWS OF THE DRAWINGS

The accompanying drawings, which are incorporated in and constitute a part of this specification, illustrate several embodiments of the invention and together with the description, serve to explain the principles of the invention.

FIG. 6 is a side view of a bi-lateral endobronchial suctioning device, with an articulating tip directed to one side using a control mechanism according to the present invention;

FIG. 7 is a side view of a bi-lateral endobronchial suctioning device with an articulating tip directed to a second side from that shown in FIG. 6 using a control mechanism according to the present invention;

FIG. 12 is a close-up view of articulation components of a catheter portion of a bi-lateral endobronchial suctioning device according to another embodiment of the present invention;

FIG. 13 is a close-up view of articulation components of a catheter portion of a bi-lateral endobronchial suctioning device with the catheter angularly articulated according to the embodiment of FIG. 12;

FIG. 14 is another close-up view of articulation components of a catheter portion of a bi-lateral endobronchial suctioning device with the catheter angularly articulated according to the embodiment of FIG. 12;

DETAILED DESCRIPTION OF THE INVENTION

In the following description of the present invention reference is made to the exemplary embodiments illustrating the principles of the present invention and how it is practiced. Other embodiments will be utilized to practice the present invention and structural and functional changes will be made thereto without departing from the scope of the present invention.

Figure 1:
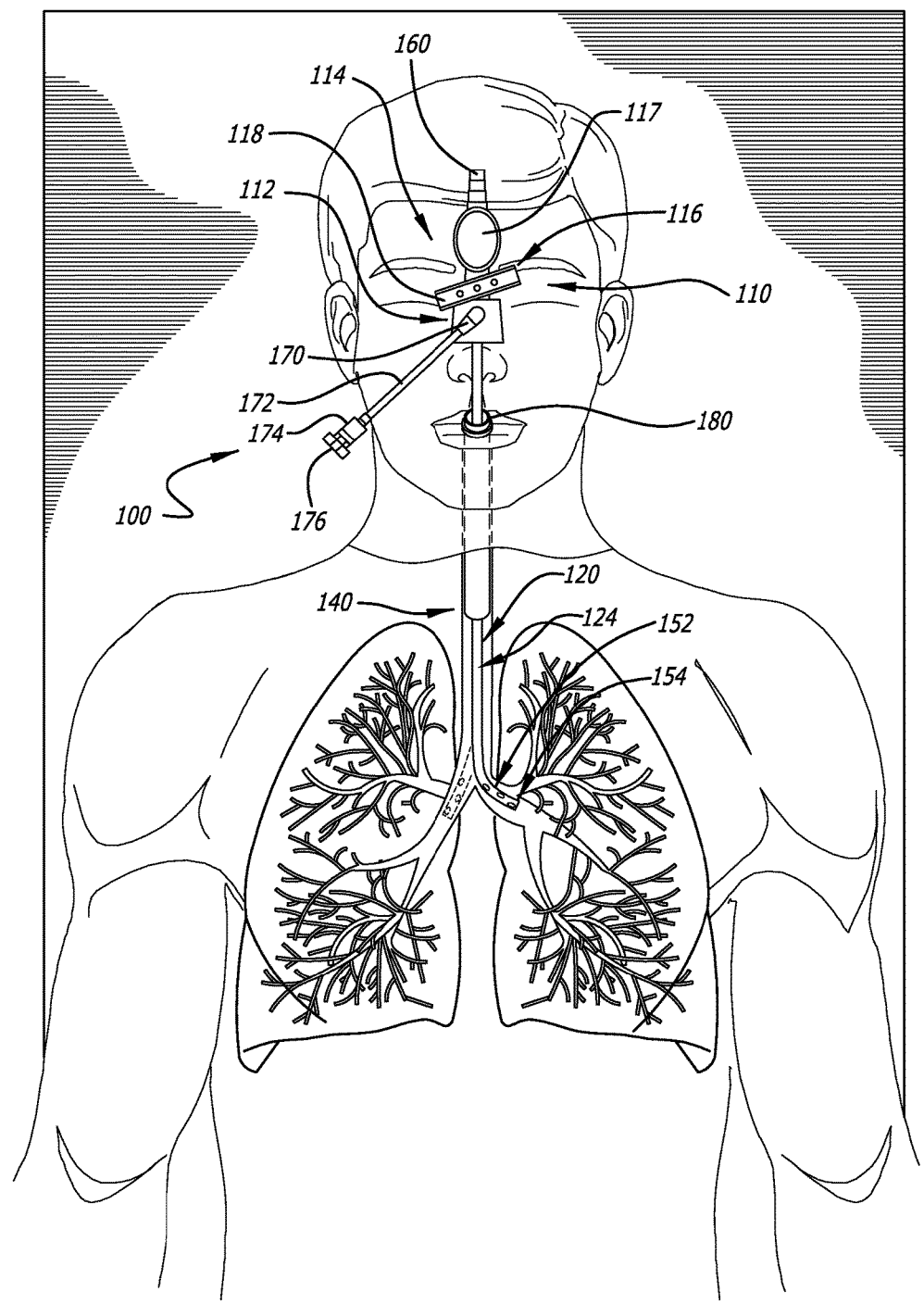
FIG. 1 is a frontal view of an intubated patient using a bi-lateral endobronchial suctioning device according to the present invention.
Figure 2:
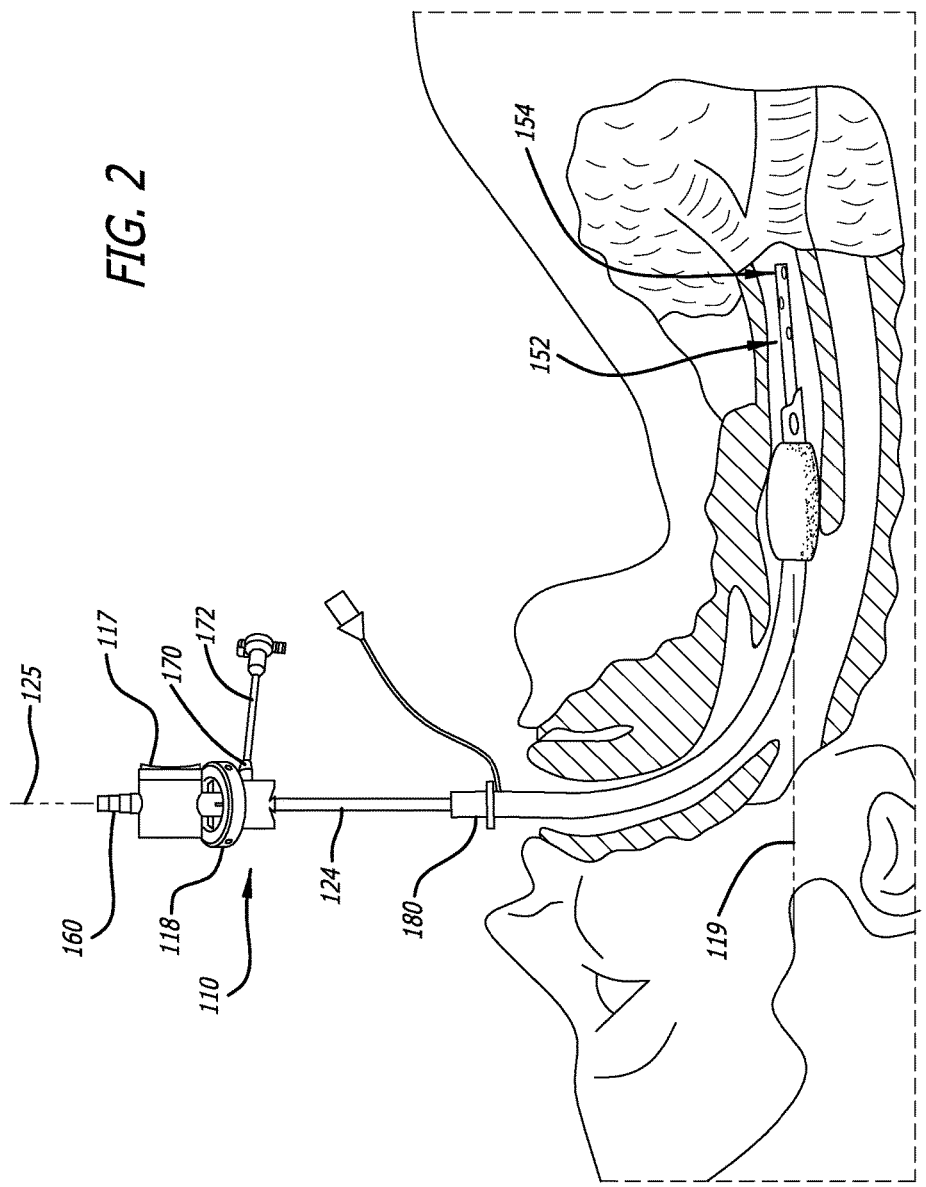
FIG. 2 is a side view of an intubated patient using a bi-lateral endobronchial suctioning device according to the present invention.

The present invention discloses a system and method of medical suctioning, in a bi-lateral endobronchial suctioning device and apparatus (BESD) 100 that is configured to enable a physician or other provider to suction both right and left bronchi of a patient's lungs in a controlled and safe manner when the patient is intubated. FIG. 1 and FIG. 2 show frontal and side views of the present invention while being deployed on an intubated patient.

Figure 3:
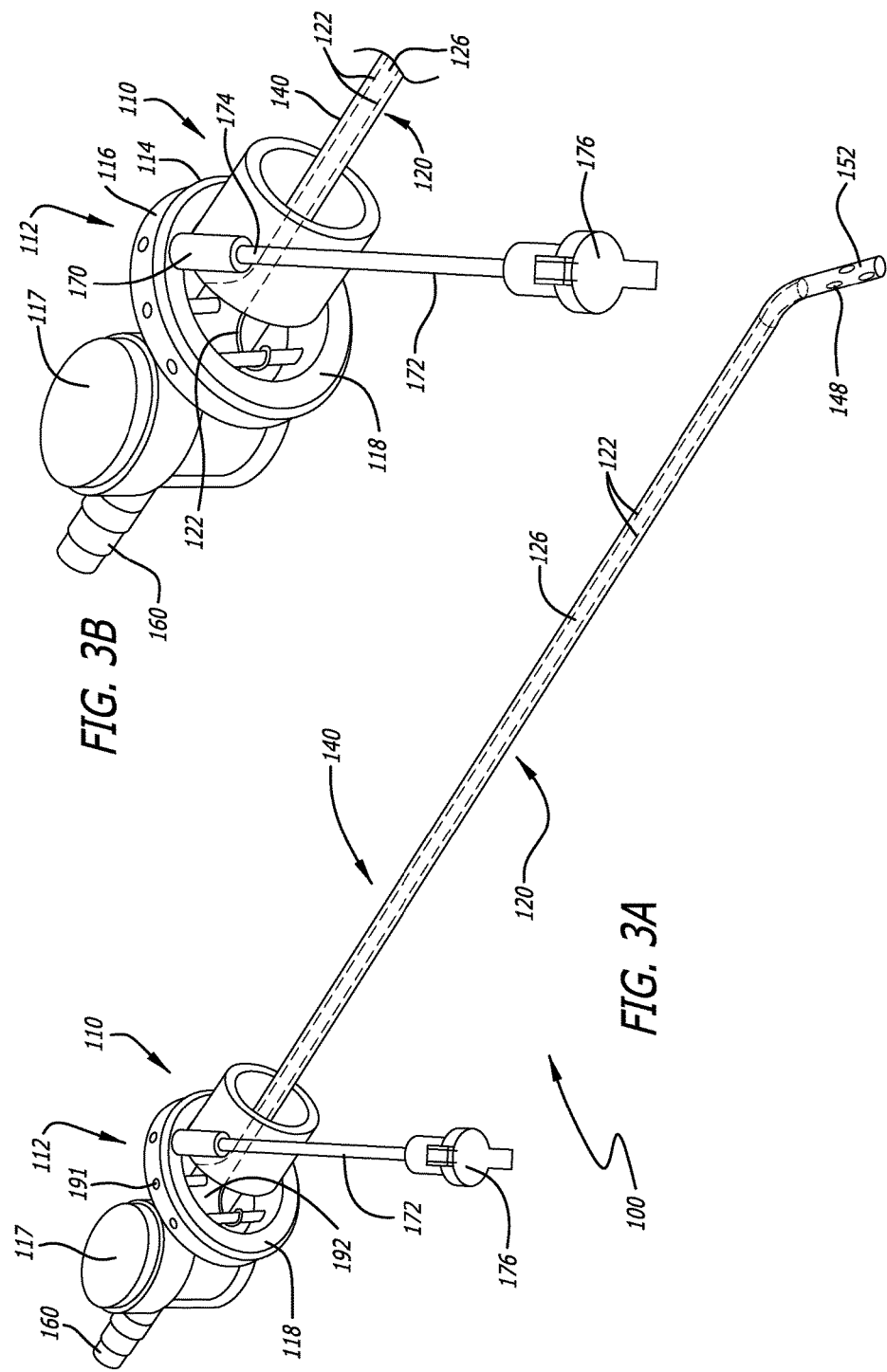
FIG. 3A is a perspective view of a bi-lateral endobronchial suctioning device according to the present invention.
FIG. 3B is an enlarged perspective view of a controller end of a bi-lateral endobronchial suctioning device according to the present invention.
Figure 4:
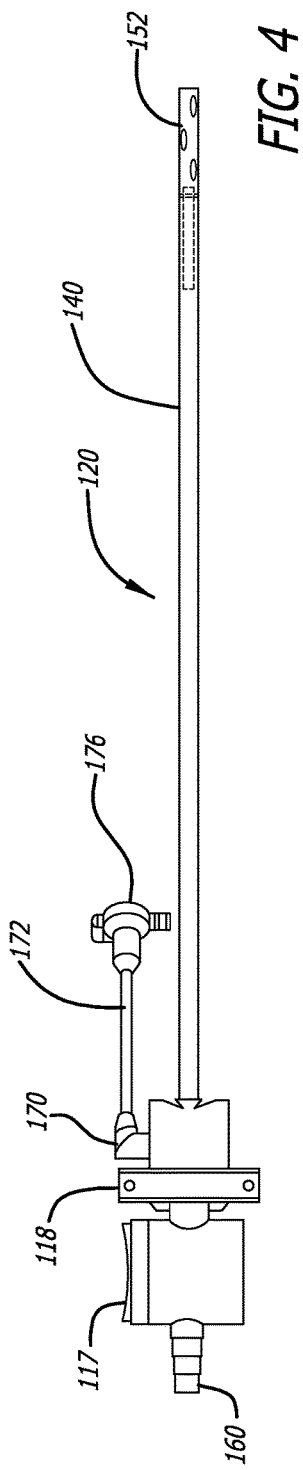
FIG. 4 is one side view of a bi-lateral endobronchial suctioning device according to the present invention.
Figure 5:
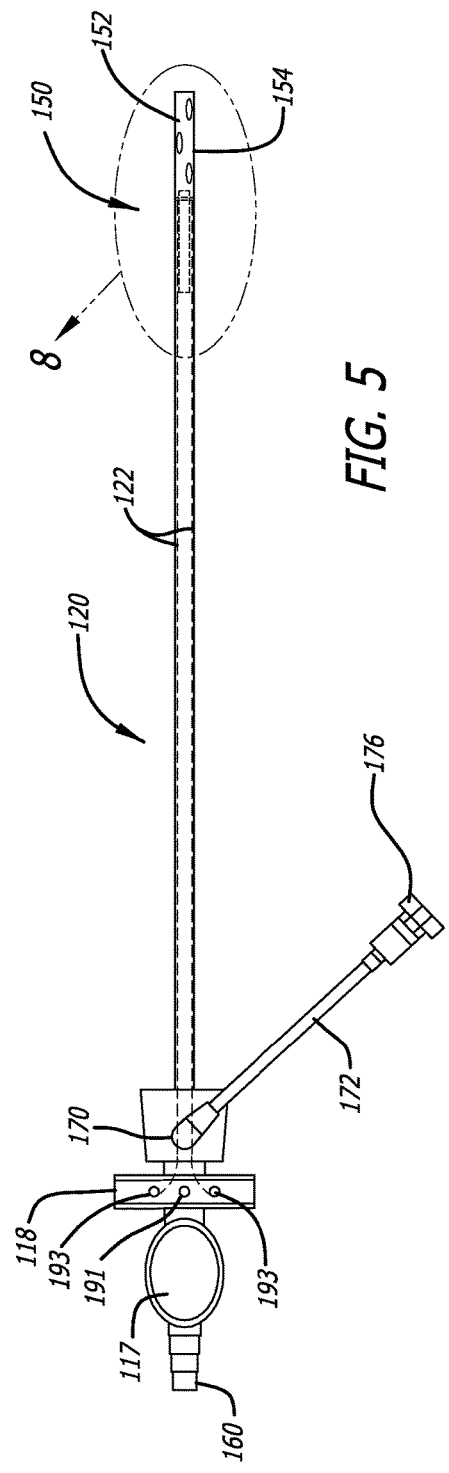
FIG. 5 is another side view of a bi-lateral endobronchial suctioning device according to the present invention.

The BESD 100 includes a control portion 110 that comprises a control interface 112 at a controller (or top) end 114. The control interface 112 is used to manipulate a control mechanism 116 that actuates one or more cables 122 within a catheter suctioning portion and system 120. The one or more cables 122 are disposed within or around a lumen, or shaft, 126 of a catheter 124. The catheter suctioning portion and system 120 also include one or more tubes 140 that together form the catheter 124. The one or more cables 122 enable a provider to maneuver and manipulate a tip 152 of an articulation portion 150 at a distal bottom end 154 of the BESD 100. FIG. 3A is a perspective view of the bi-lateral endobronchial suctioning device according to one embodiment of the present invention, and FIG. 3B is an enlarged perspective view of a controller end of a bi-lateral endobronchial suctioning device. FIG. 4 and FIG. 5 show side views of the bi-lateral endobronchial suctioning device.

The control mechanism 116 enables a provider to flex the articulating tip 152 of the articulation portion 150 in multiple directions to enable suctioning of both sides of the lungs of an intubated patient. This allows for directional control of the suctioning catheter system 120. A button 117 on the control mechanism 116 allows the provider to initiate and terminate bronchial or other suctioning with the BESD 100 once the control mechanism 116 has been actuated to maneuver the articulating tip 152 as desired in the lungs or trachea. A suction nozzle 160 is positioned at the controller end 114 for attachment to an external device into which fluids or secretions are to be suctioned from the patient using the BESD 100. The BESD also includes a bronchoalveolar lavage (BAL) port 170 coupled to the catheter suctioning portion 120.

The BESD 100 is configured so as to be insertable for use with an endotracheal tube 180 or similar device. A provider inserts the catheter 124 into the endotracheal tube 180, and then uses the top control interface 112 to articulate the tip 152 at the distal bottom end 154.

The top control interface 112 at the controller or top end 114 includes several components configured to actuate the articulating tip 152 via the articulation portion 150 at the bottom distal end 154. The control mechanism 116 is one such component, which in one embodiment is a circular disk 118 with a hollow center so as to form a ring which surrounds an upper portion of the BESD 100 at or near the top end 114. The circular disk 118 is positioned near, and in one embodiment sits just below from, where the button 117 is located. The circular disk 118 has components which couple to the BESD 100 at the upper portion in different configurations, as noted below.

The disk 118 is manipulated by the provider in an up or down manner substantially consistent with a longitudinal plane 125 in which the catheter 124 and the BESD 100 itself lie, as shown in FIG. 6 and FIG. 7. The disk 118 may also be configured to move in rocking manner at slight angles to this up or down movement relative the longitudinal plane 125.

The circular disk 118 of the BESD 100 is therefore also configured to move angularly relative to its own horizontal axis 119. The circular disk 118 is capable of pivoting, or rocking up or down, depending on which direction the provider wants an articulation of the distal bottom end 154 of the BESD 100 to be directed. The top control interface 112 therefore include means for enabling this up, down, and angular movement of the circular disk 118.

The control mechanism 116 includes actuation components 190, such as a pin 191 in a center portion 192 thereof, running through the horizontal axis 119 relative to the shape of the circular disk 118 and connecting the control mechanism 116 to the rest of the suction catheter portion 120. This pin 191 acts as a fulcrum for the angular movement of the circular disk 118. The pin 191 may run through the catheter 124 at or near the top end 114, but in other embodiments, the pin 191 may be configured so that it does not penetrate all the way through, as the catheter 124 itself may block passage of the pin 191. The circular disk 118 may also include two additional pins 193 which run along the same axis and are on opposite sides of the main fulcrum pin 191. The additional pins 193 allow one or more wires 194 (not shown) forming the cables 122 to flex, which drives the depth of articulation at the articulating tip 152 at distal bottom end 154.

Figure 17:
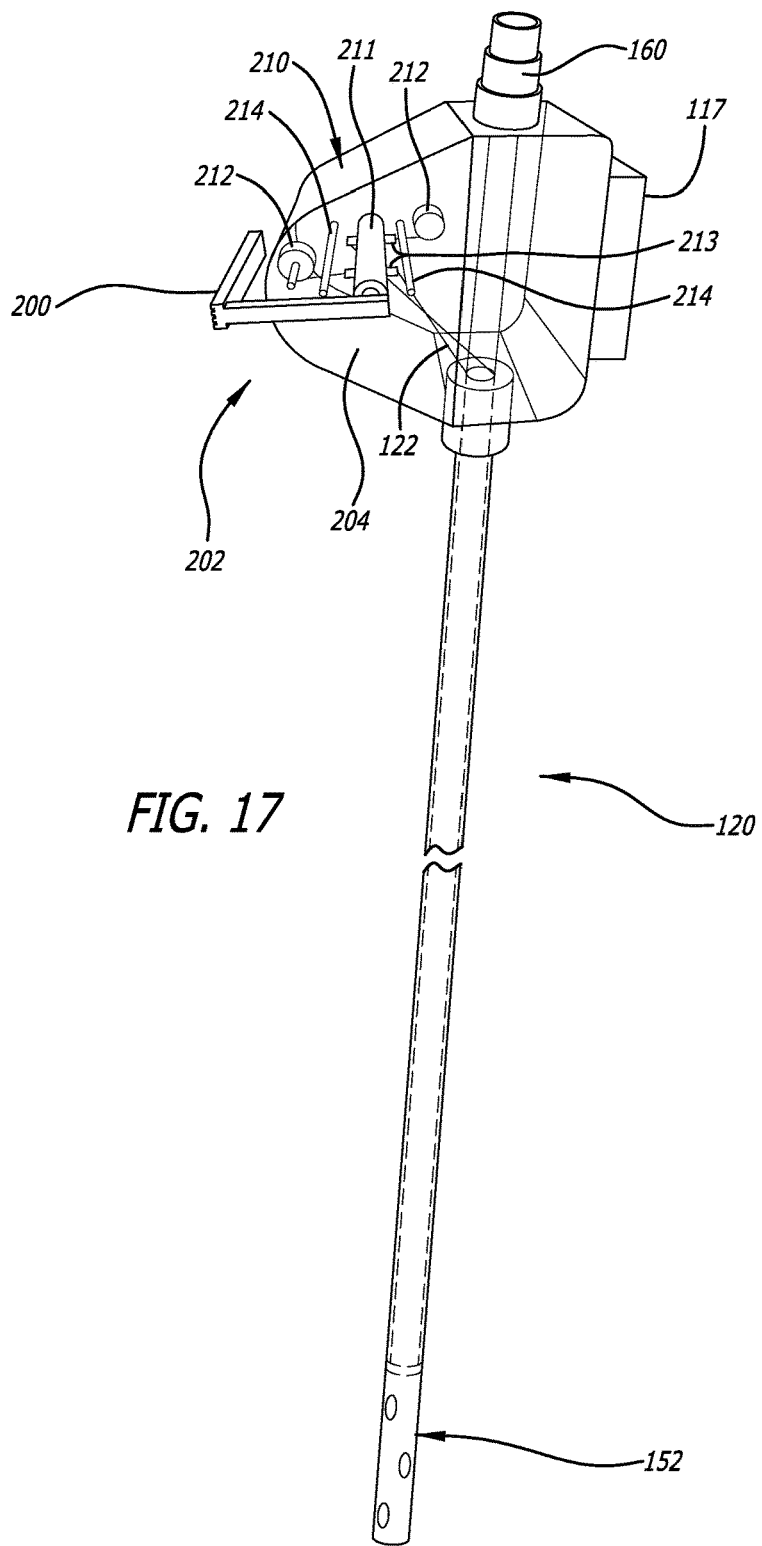
FIG. 17 is a perspective view of interface components of a bi-lateral endobronchial suctioning device according to another embodiment of the present invention.
Figure 18:
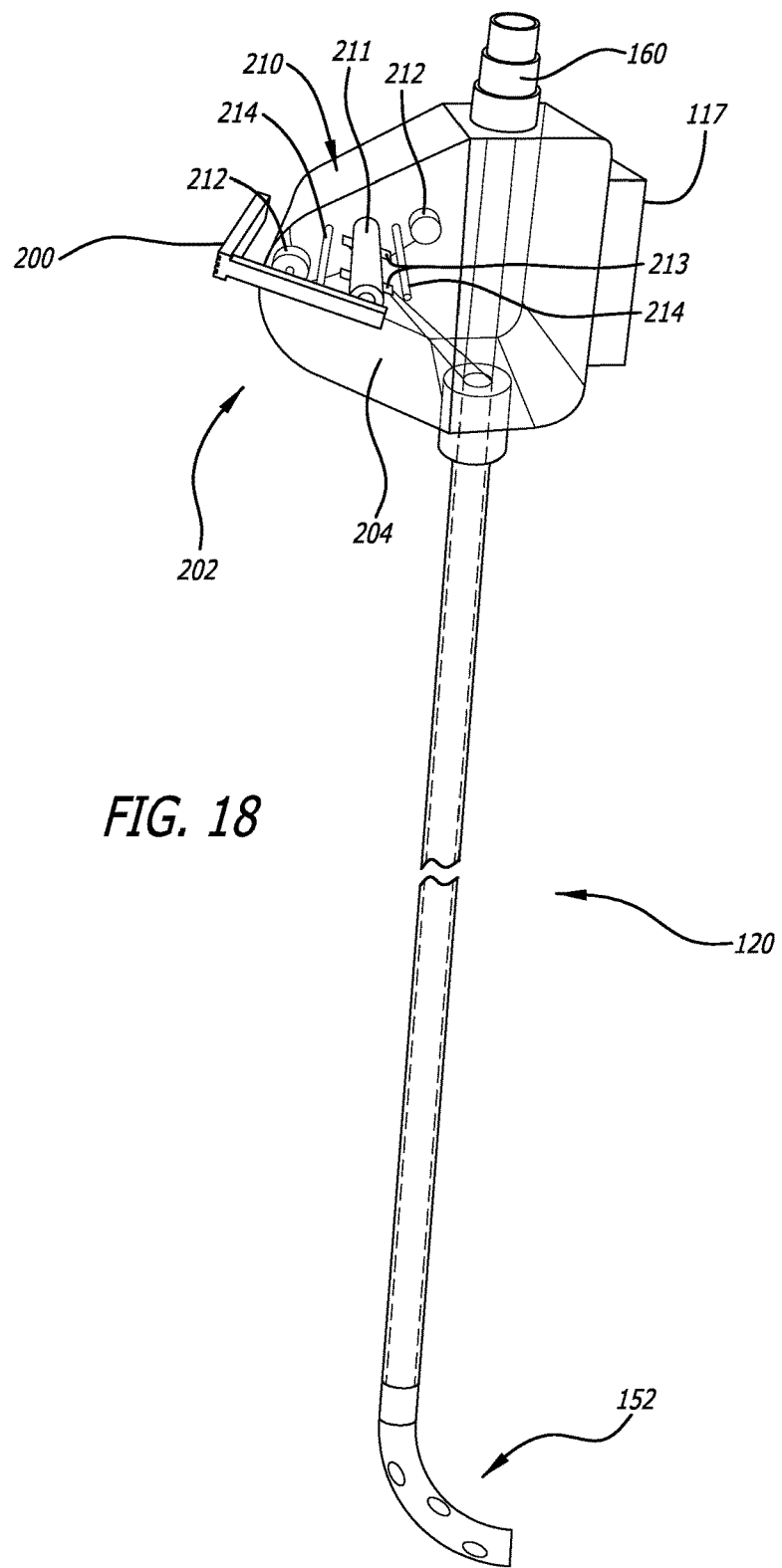
FIG. 18 is a perspective view of interface components of a bi-lateral endobronchial suctioning device articulating a distal tip to one side according to the embodiment of FIG. 17.
Figure 19:
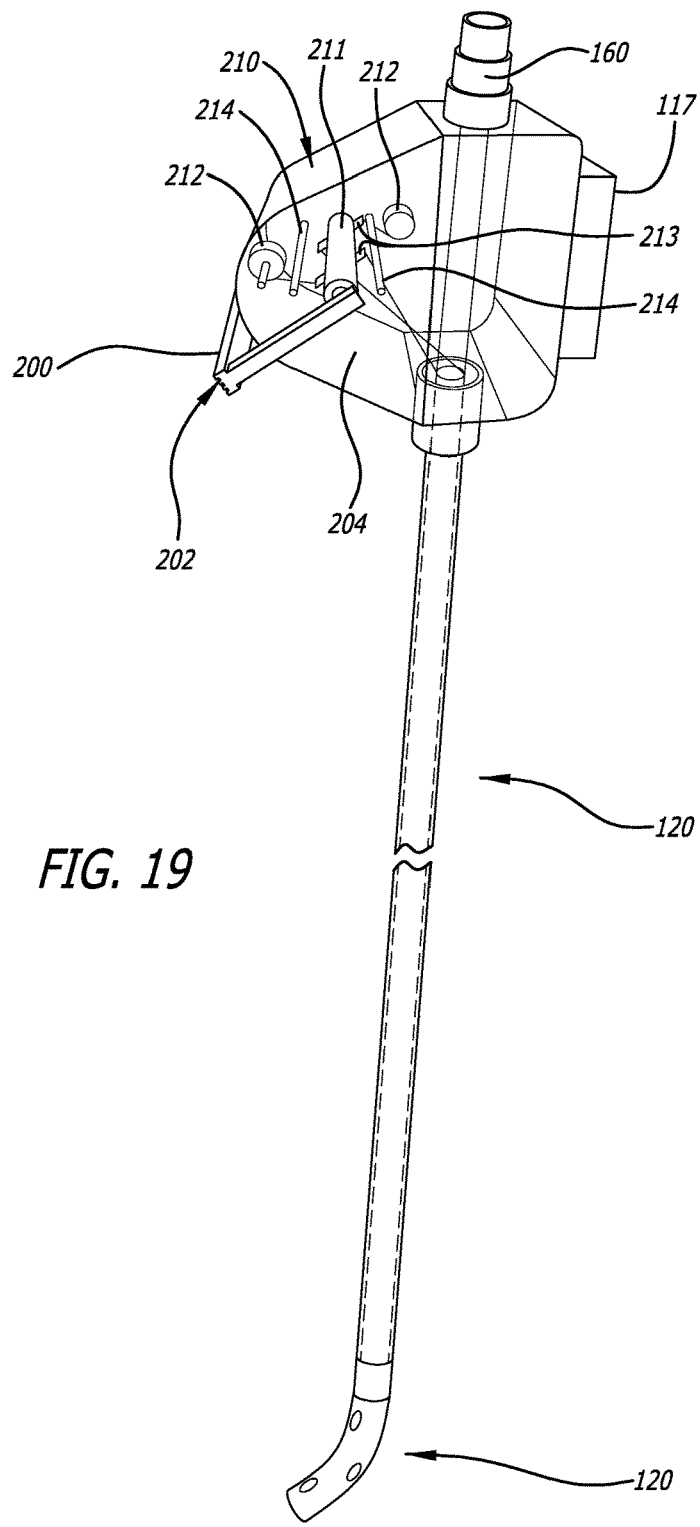
FIG. 19 is a perspective view of interface components of a bi-lateral endobronchial suctioning device articulating a distal tip to another according to the embodiment of FIG. 18.

In one embodiment of the present invention, the control mechanism 116 may comprise a control lever 200 and a cylindrically-shaped housing 202 that is the structure holding all of the components 210 actuated by the control lever 200. The control lever 200 is actionable from an outside 204 of the housing 202, and can be either depressed or elevated to cause articulation of the articulating tip 152 at the distal bottom end 154 of the suction catheter 124. FIG. 17 shows this embodiment of the BESD 100, and FIG. 18 and FIG. 19 demonstrate the actuation of the control lever 200 and the articulation of the distal bottom end 154 to either side.

Inside the housing 202 are the actuation components 210 which work in synchronicity with the control lever 200 to cause the distal tip articulation 152 according to this embodiment. One actuation component 210 is a rod 211 which the control lever 200 attaches to, and which turns clockwise or counter-clockwise depending on which direction the control lever 200 is elevated or depressed respectively by the provider. The rod 211 has two small holes which are elongated horizontally in relation to the suction catheter system 120. The one or more cables 122, which attached to the distal articulating tip 152 of the suction catheter 124, run along the sides of the suction catheter 124 on opposing sides, enter the housing 202, and pass through the small holes in the rod 211. The holes allow torque to occur in order to cause articulation of the distal articulating tip 152. Each cable 122 is re-oriented 90 degrees as it enters the housing 202 of the BESD 100 before entering the elongated holes in the rod 211. After passing through the holes, they couple to a small coil spring 212 on either side. This configuration allows the cables 122 to have some flexibility when the control lever 200 is not actuated. As the control lever 200 is elevated or depressed by the provider, the cables 122 begins to wind around the rod 211, so that one cable 122 tightens and the other loosens. This translates into a pull/loosening motion at the distal articulating tip 152 of the suction catheter where the string/cables attach.

As noted above the coil springs 212 are disposed on opposing sides of the rod 211, which also may include two dowels 213 perpendicularly inserted in the holes in the rod 211 in another embodiment of the present invention. Two wire guide cylinders 214 are positioned parallel to the rod 211, and each cable 122 passes through a wire guide cylinder 214, and a dowel 213 so that the cable 122 passes perpendicularly through the holes in the rod 211, guided by the wire guide cylinder 214. Upon exiting each dowel 213, the cables 122 extend and are inserted into the catheter 124 on opposing sides thereof. In a further alternative embodiment, a cable 122 is simply attached to the rod 211 at some point, either at a vertical cross-beam attached to the rod 211 or simply wrapped around the rod 211 only in order to allow the desired articulating depth.

Figure 8:
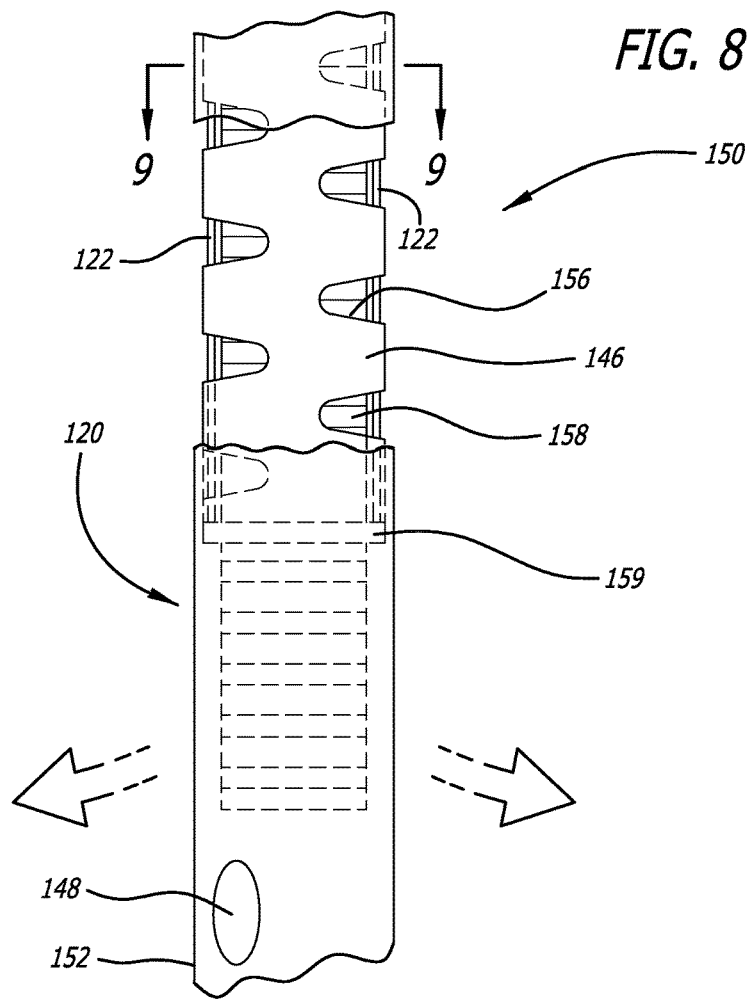
FIG. 8 is a close-up view of a catheter portion of a bi-lateral endobronchial suctioning device according to one embodiment of the present invention.
Figure 9:
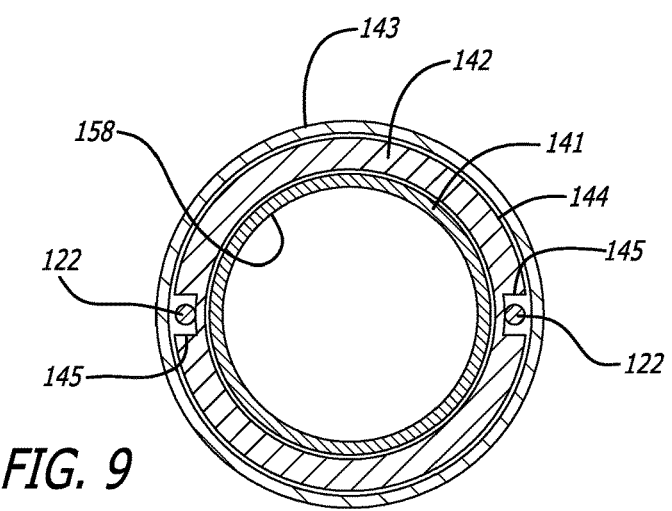
FIG. 9 is a cross-sectional view of the catheter portion of FIG. 8.
Figure 10:
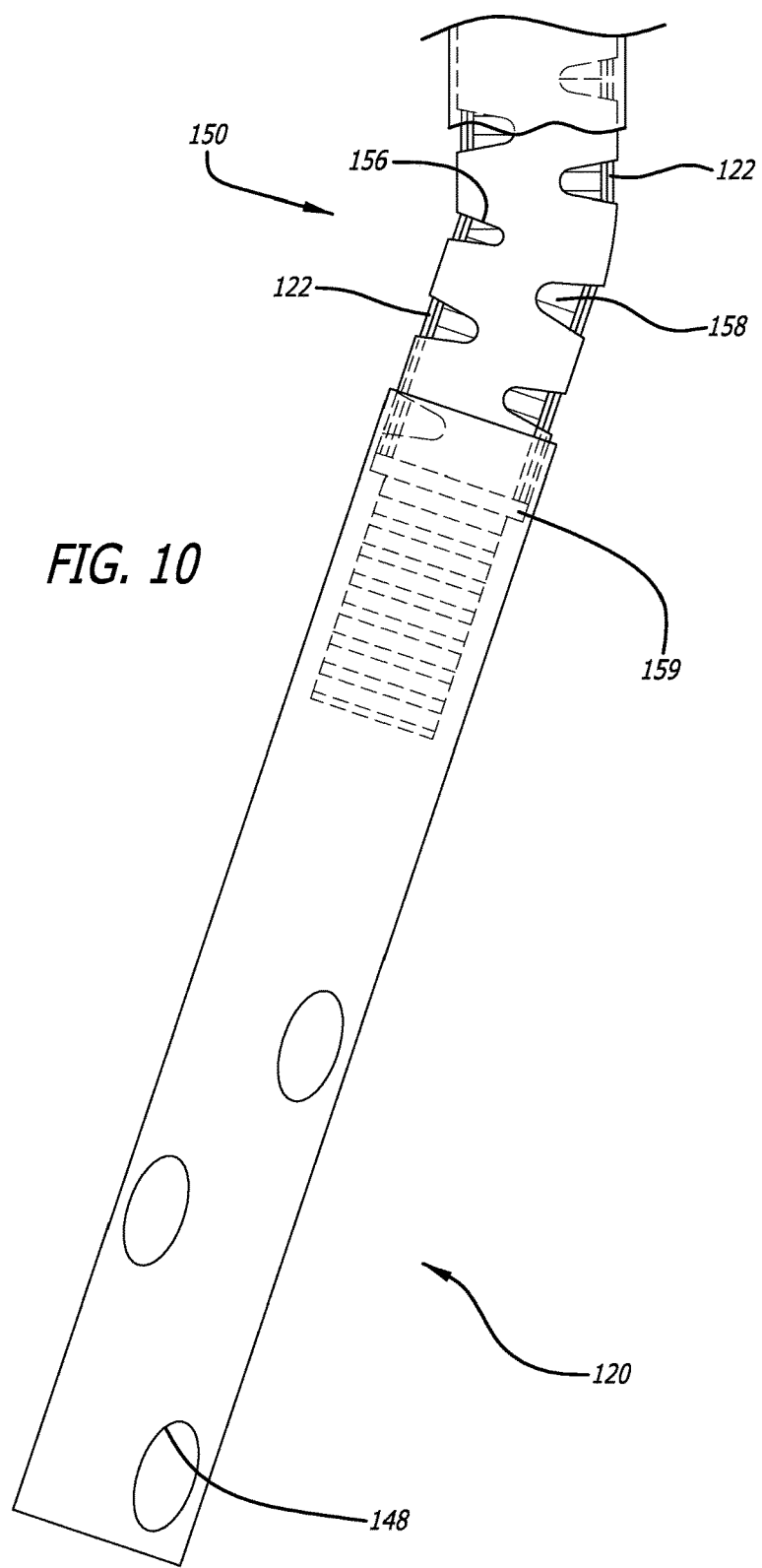
FIG. 10 is a view of a catheter portion articulated to one side according to the embodiment of FIG. 8.
Figure 11:
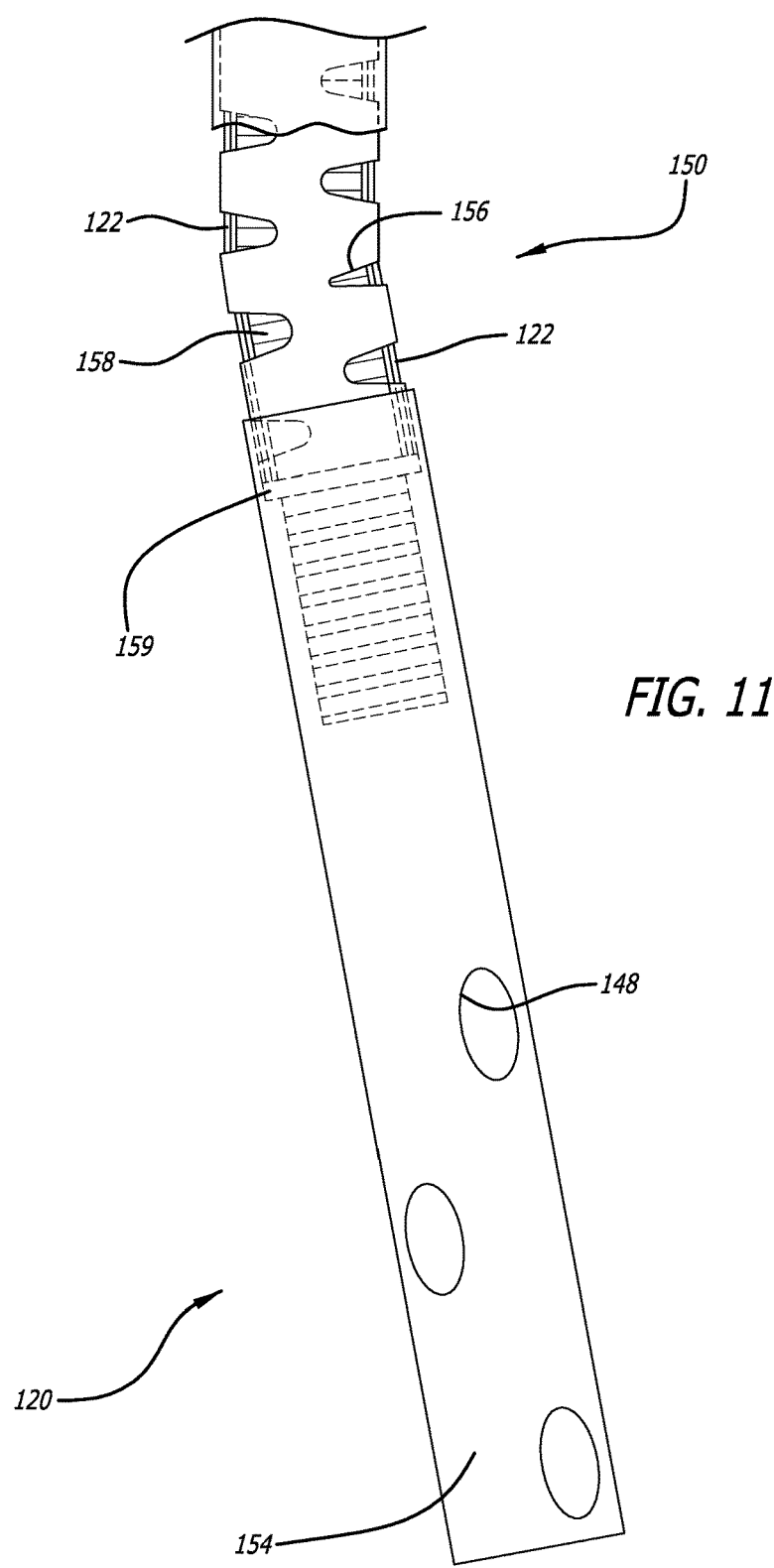
FIG. 11 is a view of a catheter portion articulated to another side from that of FIG. 10, according to the embodiment of FIG. 8.

FIG. 8 through FIG. 11 are various views of a catheter 124 of the BESD 100 according to one embodiment of the present invention. FIG. 8 is a close-up of the one or more tubes 140, and FIG. 9 is a cross-sectional view of the tubes 140. FIG. 10 and FIG. 11 show the catheter 124 articulated to different sides by the control mechanism 116.

The one or more tubes 140 that together form at least a substantial portion of the catheter 124 may include an inner tube 141, a middle tube 142, and an outer tube 143. Regardless of the embodiment, it is contemplated there are multiple layers of catheter tubing, with a cable 122 running either in between or through them. This forms a "catheter inside a catheter" appearance as in FIG. 8. Where there are three tubes, they form a three-ply catheter arrangement, with the outer-most layer forming a layer or sheath extending all the way from top to bottom of the catheter 124.

In one embodiment, the cables 122 are positioned within the lumen 126 of the catheter 124 to run along an outer surface 144 of a middle tube 142, between the middle tube 142 and the outer tube 143. The cables 122 may be positioned to run along a plurality of grooves, channels, or recesses, 145 in the outer surface 144 to keep them in place as they run along the outer surface 144. The grooves, channels, or recesses 145 may extend along a significant portion of the outer surface 144 of the middle tube 142, or may be periodically situated thereon. Holes may also be positioned within walls of the catheter 124 for the cables 122 to pass through.

The BESD 100 includes an articulation joint portion 150, which enables the catheter 124 to be actuated to move the articulating tip 152 at the distal bottom end 154 as needed. Several manifestations of this articulation joint portion 150 are contemplated, and are within the scope of the present invention. For example, in one embodiment of the present invention, one or more "nicks" or grooves 156 are made in one or more of the tubes 146 forming the catheter 124 to allow the tube 140 to bend where those nicks 156 are positioned. As shown in FIG. 8, FIG. 10, and FIG. 11, these nicks/grooves 156 are on the middle tube 142, with the outer tube 143 forming a sheath over the middle tube 142. A spring coil 158 may or may not form at least a part of the inner tube 141 and runs along an inside surface 147 of the catheter lumen 126 and near to where the nicks and grooves 156 are positioned in the catheter 124, which imparts strength to the catheter 124 and to help spring the catheter 124 back to its original form when the provider ceases actuating the control mechanism 116.

FIG. 12, FIG. 13, and FIG. 14 show an alternative embodiment, in which the articulation joint portion 150 comprises a plurality of fitted articulation pieces 157 forming part of the middle tube 142. In this embodiment, the cables 122 run through the fitted articulation pieces 157 along holes or grooves in the outer surface of the middle tube 142. The plurality of fitted articulation pieces 157 are form-fitting relative to each other, and perform a rocking movement when the control mechanism 116 is actuated, causing articulation to occur in the articulating tip 152 at the distal bottom end 154. The fitted articulation pieces 157 may also have grooves 156 between them which allow them a greater degree of movement. The cables 122 end at the last fitted articulation piece 157. In still another alternative embodiment, the catheter 124 may include just a spring forming at least a part of the inner tube 141, with no nicks or grooves 156 in the middle tube 142. In still another embodiment, the inner 141 tube acts as a spring and only extends so far as to span the articulating joint portion 150 itself.

Other features of the present invention are also contemplated. For example, the outer tube 143 may include one or more orifices 148 on the surface thereof, and at or near the bottom distal end 154, to enable suctioning through the catheter 124. These orifices 148 are shown for example in FIG. 3A, FIG. 4, FIG. 5, FIG. 6, FIG. 7, FIG. 10, FIG. 11, and in FIGS. 15-19. In another embodiment, the articulation joint portion 150 may also include a ring 159 positioned roughly a few centimeters up along the catheter 124 from the terminus of the distal bottom end 154. The one or more cables 122 are coupled to, and end at, this ring 159, which is rotatable when the provider actuates the control mechanism 116 to articulate the articulating tip 152. The ring 159 is positioned at a point along a length of the catheter 124, referenced from the top controller end 114, to where the middle tube 142 ends, and the one or more nicks or grooves 156 also end, to anchor the one or more cables 122 within the catheter 124.

Referring to FIG. 1, FIG. 2, FIG. 3A and FIG. 3B, and as noted above, the BESD 100 also includes a bronchoalveolar lavage port (BAL) port 170 that allows fluids, solutions, or medications, such as for example sterile saline, to travel down the catheter 124 in order to assist with breaking up thick secretions which collect in the airways of intubated patients. The BAL port 170 may be located at various positions along the catheter 124, such as for example near the top control interface 112 and near to where the control mechanism is actuated, which is where a provider's hands would be placed when operating the BESD 100.

Figures 15, 16:
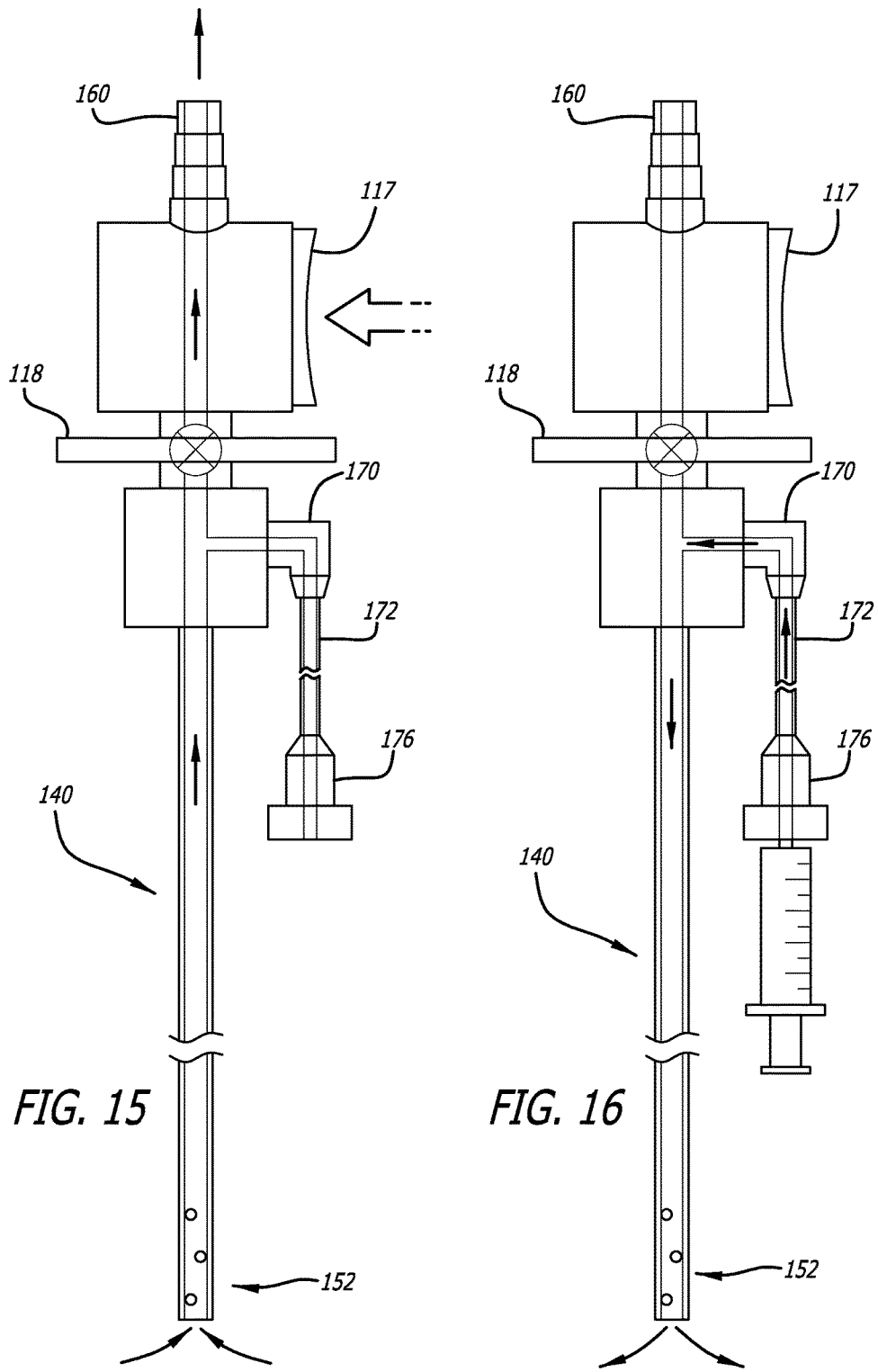
FIG. 15 is a diagram of a bi-lateral endobronchial suctioning device showing a flow of fluids out of the device upon actuating a button according to one embodiment of the present invention.
FIG. 16 is a diagram of a bi-lateral endobronchial suctioning device showing a flow of fluids into the device with the use of a bronchoalveolar lavage (BAL) port according to one embodiment of the present invention.

Without a BESD 100, sterile saline is simply squirted down an endotracheal device, which provides no directionality to where the sterile saline is going. However, with the directional capability of the BESD 100 of the present invention, the BAL port 170 enables sterile saline to go directly to the area of the airways that are to be suctioned. The BAL port 170 therefore communicates with the main suction catheter 124 to allow fluids such as saline to go into a specific area, wherever the distal bottom end 154 of the main suction catheter 124 lies. FIG. 16 shows the flow of fluids into the BESD 100 using the BAL port 170.

In one embodiment, the BAL port includes a small tubular extension 172, with a cap 176 on an end 174 of the tubular extension 172. The cap 176 prevents air from escaping while suctioning, and together the extension 172 and cap 176 operate to keep the BESD 100 a closed system. The cap 176 may be removed after the BESD 100 has been deployed into a patient's lung, and a syringe can be attached to the tubular extension 172 so that saline can be squirted down the catheter 124 through the BAL port 170. The extension 172 communicates with the main catheter 124 so that when saline enters the BAL port 170 it also enters the catheter 124, it flows into the lung. The provider then closes the cap 176 and begins suctioning out the lung that now has that saline in it with the BESD 100.

Figure 20:
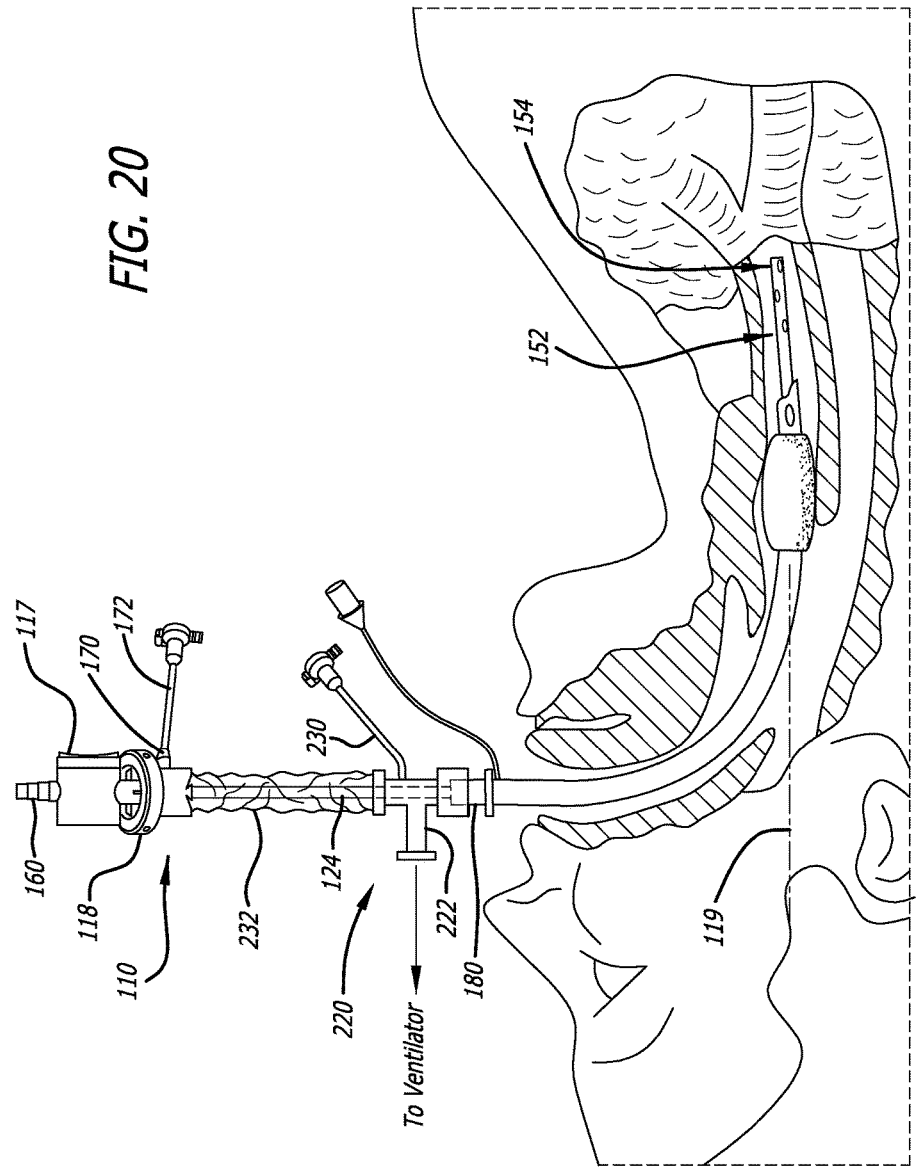
FIG. 20 is another side view of an intubated patient using a bi-lateral endobronchial suctioning device according to another embodiment of the present invention.

Referring to FIG. 20, the BESD 100 may also include a manifold 220 that provides a means of attachment to a ventilator machine, to the end of an endotracheal tube 180, and to a catheter cleaning and irrigation system. The manifold 220 therefore acts as a means to keep the patient on a ventilator while at the same time giving the provider the ability to suction the patient. The catheter cleaning and irrigation system includes a cleaning catheter 230 and also includes a sterile sleeve 232 which keeps the catheter 124 sterile while it is not being deployed into the patient. A port 222 at the attachment point of the manifold 220 to the BESD 100 may be provided to couple the BESD 100 to a ventilator machine. Such a "BAL like" port 222 is not to be confused with an actual BAL port 170, because it is not used for bronchoalveolar lavage. If a clean, new suction catheter 124 is needed, the BESD 100 may be detached from the manifold 220 and a new BESD 100 may be re-attached. This attachment point therefore forms a chamber where the catheter cleaning and irrigation system attaches.

In one additional embodiment of the present invention, the manifold 220 may be a separable component from the suction catheter portion 120, so that the two can be disconnected from each other at an attachment point. A cap may also be included to cover the entrance to the manifold when not coupled to the suction catheter portion 120. In another embodiment, the catheter components are not detachable from the manifold 220, so that together they form a single unit. A housing may be used to connect to the manifold 220 for the purposes of guiding the suction catheter down the endotracheal tube 180. Regardless, it is to be understood that the BESD 100 may be designed where it is permanently attached to a manifold 220 or removably attached to a manifold 220, so that a chamber is formed to which a separate catheter cleaning and irrigation system or ventilator may be attachable to the entire BESD 100.

As noted above, the BESD 100 includes a suctioning system which enables it to suction secretions from an intubated patient's lung. This suctioning system includes, in addition to the catheter 124, a button 117 at the interface portion 112 near the top end 114, and a suction nozzle 160 through which secretions or fluids from the left and right bronchi of an intubated patient exit the BESD 100.

FIG. 15 is a diagram of the bi-lateral endobronchial suctioning device showing a flow of fluids out of the BESD 100 upon actuating the button 117. The button 117 therefore acts as a toggle to allow the provider to initiate and terminate suctioning using the BESD 100. It is contemplated that such initiating and terminating suctioning may be performed by other components, such as a switch or a lever, and therefore button 117 is but one of many styles and shapes of components which may be used to actuate suctioning in the BESD 100.

The BESD 100 may also include one or more components that enable connection and use with systems and devices such as an ultrasound machine, for example on a patient's chest, to locate the tip of the catheter 124 inside a lung field. The BESD 100 may therefore include a hyperechoic component in the articulating tip 152 of the suction catheter 124, so that an ultrasound probe could easily detect and see the articulating tip 152. One example of a hyperechoic component may be one or more thin metal strips or pieces embedded or otherwise located inside the articulating tip 152 at the distal bottom end 154 of the catheter 124 to cause it to be hyperechoic. In another embodiment, the articulating tip 152 may include an anode, and small sensors may be placed on the chest wall of the patient, for example near the nipples, so that when the catheter 124 is close to one of the sensors, a light or other indicator is activated to show that the catheter 124 is in the left or right bronchus. Such a configuration enables certainty as to which bronchus of the lung the catheter 124 is located and aids in articulating the BESD 100.

As indicated above, the BESD 100 may therefore also be configured for use with an ultrasound machine in the field of pulmonology. The catheter 124 in this embodiment may be utilized with ultrasound technology to locate and biopsy lung tumors, with the ultrasound device enabling a determination of which lung field the catheter 124 of the BESD 100 has been articulated in.

The present invention may also include a method of removing built-up secretions in the lungs or other areas of an intubated patient. The method utilizes a device 100 configured for bilateral insertion into an intubated patient's lungs, and includes actuating a control mechanism 116 on the device to manipulate a plurality of cables 122 from a controller end 114 that pass through a catheter portion 120, and articulating a joint portion 150 in the catheter portion 120 so that angular movement of the control mechanism 116 flexes an articulating tip portion 152 at a distal end 154 opposite the controller end 114 into both a left bronchus and a right bronchus of the intubated patient's lungs as desired. The method also includes suctioning the patient's lungs by actuating components to initiate and terminate the removal of bronchial secretions from the intubated patient.

The foregoing descriptions of embodiments of the present invention have been presented for the purposes of illustration and description. It is not intended to be exhaustive or to limit the invention to the precise forms disclosed. Accordingly, many alterations, modifications and variations are possible in light of the above teachings, may be made by those having ordinary skill in the art without departing from the spirit and scope of the invention. It is therefore intended that the scope of the invention be limited not by this detailed description. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

The invention claimed is:

1. A medical suctioning system, comprising:
   a device configured for bilateral insertion into an intubated patient's bronchi, the device including
   1) actuating components that include a control mechanism coupled to a plurality of cables at a controller end;
   2) catheter components that include a plurality of layered tubes comprising an inner tube, a middle tube, and an outer tube, the plurality of cables either running along a surface of the middle tube from the controller end and protected by the outer tube, or imbedded in holes in walls of one tube in the plurality of layered tubes;
   3) articulating components that include an articulation joint portion formed in a portion of the middle tube comprising the catheter components and actionable by the plurality of cables so that angular movement of a control disk flexes an articulating tip portion at a distal end opposite the controller end into both a left bronchus and a right bronchus of the intubated patient as desired;
   4) suctioning components at the controller end that include a button to initiate and terminate suctioning of the bronchial secretions from the patient, and a nozzle through which secretions exit the device after bronchial suctioning;
   5) cleaning components at least comprising a cleaning catheter attached to a manifold through which fluids are inserted to clean the catheter components of secretion buildup; and
   6) a sterile sleeve which attaches to a cleaning end of the manifold to keep a suction catheter sterile while not deployed in a patient.

2. The medical suctioning system of claim 1, further comprising bronchoalveolar lavage components that include a tubular extension coupled to a port configured in a side of the catheter components for bronchoalveolar lavage of the intubated patient, and through which a fluid is applied to the catheter components to flow into the lung, and a cap to prevent air from entering the catheter components when removing secretions from the lungs of the intubated patient.

3. The medical suctioning system of claim 1, wherein the device is insertable into an endotracheal tube for use on the intubated or trached patient.

4. The medical suctioning system of claim 1, wherein the articulating tip portion includes one or more components that enable the distal end to be detected by an external probe from one or more of an ultrasound device or by an anode or a magnet.

5. The medical suctioning system of claim 2, wherein the articulating tip portion includes one or more orifices at or near the distal end that enable suctioned secretions to pass through the catheter components.

6. The medical suctioning system of claim 1, wherein the articulating components include a spring extending around at least a portion of the articulating joint portion.

* * * * *